United States Patent [19]

Ross et al.

[11] Patent Number: 5,690,968
[45] Date of Patent: Nov. 25, 1997

[54] ANALGESIC ANAESTHETIC COMPOSITIONS

[75] Inventors: John Alexander Strachan Ross, Aberdeen; Michael Eric Tunstall, Stonehaven, both of Scotland; Robert Colin Rodgers, Carlisle, England

[73] Assignee: Aberdeen University, Aberdeen, Scotland

[21] Appl. No.: 537,809

[22] PCT Filed: Apr. 21, 1994

[86] PCT No.: PCT/GB94/00839

§ 371 Date: Oct. 31, 1995

§ 102(e) Date: Oct. 31, 1995

[87] PCT Pub. No.: WO94/23727

PCT Pub. Date: Oct. 27, 1994

[30] Foreign Application Priority Data

Apr. 22, 1993 [GB] United Kingdom ............ 93 08 306

[51] Int. Cl.⁶ .......................... A61K 33/00; A61K 31/08

[52] U.S. Cl. ............................................. 424/718; 514/722
[58] Field of Search ............................ 424/718; 514/722

[56] References Cited

FOREIGN PATENT DOCUMENTS 25 24 956  12/1976  Germany.

OTHER PUBLICATIONS

S. Arora et al. "Self-administered mixture of entonox and isoflurane in labour" International Journal of Obstetric Anaesthesis, vol. 1, 1992, pp. 199–202.

*Primary Examiner*—William R. A. Jarvis
*Attorney, Agent, or Firm*—Nixon & Vanderhye

[57] ABSTRACT

An analgesic anaesthetic composition comprising up to 50% v\v nitrous oxide, the balance being oxygen and another respirable gas; characterized by the addition of an analgesically effective amount of an ether-based analgesic anaesthetic disposed in a single container above its pseudo-critical temperature at a pressure of up to 2000 psi, thereby to form and maintain a homogenous analgesic composition.

5 Claims, No Drawings

ANALGESIC ANAESTHETIC COMPOSITIONS

This application is a 371 of PCT/GB94/00839 filed Apr. 21, 1994.

The present invention relates to analgesic anaesthetic compositions, and particularly to such a composition comprising about 50% v/v nitrous oxide and oxygen, sold under the Registered Trade Mark 'Entonox'.

The storage of gas mixtures in a homogenous state in a pressurized container is well established. It was shown in 1961 that a permanent gas, such as oxygen, was able to sustain nitrous oxide (a gas with analgesic and anaesthetic properties) in a homogenous gaseous admixture at temperatures and pressures at which previously part of the nitrous oxide was expected to separate out into liquid form (The Lancet 28 Oct. 1961, p 964) and in GB-A-967,930.

Following further studies, premixed nitrous oxide and oxygen at approximately 50/50 v/v mixture was made available. This was utilised for the relief of labour pains in child-birth from 1965 under the Trade Name 'Entonox'. Entonox is inhaled for self-administered inhalation analgesia via a demand regulator under medical, nursing or paramedical supervision for many applications in addition to child-birth. The fundamental advantages of premixing the gases in a single pressurized container are safety (the oxygen supply cannot fail), and simplicity (no mixing device is required).

Nitrous oxide at 50% is itself a potent analgesic agent, which after more than a minute or so of deep and rapid inhalations causes a number of patients to become amnesic, inaccessible to instructions and uncontrollable in response to strong stimuli. Its uptake and excretion are both rapid. It is because the pain of each uterine contraction of child-birth is both of such relatively short duration and is separated by a few minutes from the next pain that 50% nitrous oxide has been practical for use as an analgesic. Each episode of inhalations during child-birth is normally too short to allow amnesic levels of nitrous oxide to be reached in the brain. Nitrous oxide at a concentration of 50% is generally the lowest concentration used for women in labour and will make a number of people unresponsive if breathed for long enough. Nitrous oxide at a concentration of 30% has been used in dentistry for more prolonged times. This is probably the lowest concentration that is used.

The rapid uptake and excretion of nitrous oxide requires special understanding by those supervising the use of Entonox. For constant pain, say during ambulance transport following injury, the patient needs to be instructed in the correct intermittent use of Entonox to make the most of its advantages. When Entonox is administered for short painful procedures not requiring a general anaesthetic, such as the withdrawal of drainage tubes and certain other therapeutic procedures, it is always a problem to attain the correct timing and duration of inhalation to cover the peak of pain.

These problems suggest that an inhalation admixture with a lower concentration of nitrous oxide, but with the addition of a volatile ether-based analgesic agent such as isoflurane, would allow a longer duration of inhalation, better maintenance of co-operation and more prolonged pain relief. Such mixtures, with their slower onset and decline of analgesia, have already been shown to be beneficial.

Gas mixtures containing nitrous oxide and oxygen were covered in GB-A-967930 (1961). Included in that disclosure was the use of the volatile anaesthetic agent Halothane at up to 1% as an adjuvant to the admixture. Halothane is a volatile non-analgesic anaesthetic agent which however has been shown to be unstable in the presence of light, oxygen and metal (see British Journal of Anaesthesia, 1984, Volume 56, Supplement 3s to 7s; R. C. Terrell).

It has recently been shown that the inhalation of Entonox, with the separate addition of 0.25% isoflurane vapour, provides more relief for the pains of childbirth than Entonox alone (International Journal of Obstetric Anaesthesia 1992, Vol 1 p199–202). Isoflurane is a volatile ether-based analgesic anaesthetic agent. In this disclosure, isoflurane was added to Entonox via a vaporiser in line with the breathing hose from the demand regulator. For general surgical anaesthesia, isoflurane is normally utilised at concentrations of 0.5 to 1.5% rising to 1.5 to 3%, usually in combination with various other medications. It is always administered via its own separate vaporiser.

Isoflurane, for example, is 1-chloro-2,2,2-trifluoroethyl difluoromethyl ether and hence has a molecular configuration and molecular weight (185) which indicates that an evenly distributed gaseous admixture with Entonox cannot be achieved at the necessary concentrations at normal filling pressures for medical gas cylinders.

Moreover at 2000 psi the theoretical maximum of isoflurane which would admix is below about 0.2%; a level which is too low for significant analgesia. Further, this limit is significantly reduced if the ambient temperature of the stored admixture falls from 20° C. to say 5° C. during heavy use of the cylinder, the temperature may also fall below the pseudo-critical temperature of the admixture. The pseudocritical temperature is the temperature above which any component of the gaseous mixture can not be compressed to a liquid.

The inventors have now discovered that ether-based analgesic anaesthetics in fact successfully admix evenly above their theoretical maxima, and further that the pseudo-critical temperature of admixtures of nitrous oxide and oxygen rise significantly in the presence of small amounts of the said ethers.

Thus at below 0.4% v/v isoflurane vapour the admixture is in fact evenly distributed and also at that level the isoflurane has a significant analgesic, as opposed to anaesthetic effect, allowing if desired a reduction of the percentage of nitrous oxide. Other ether-based analgesic agents suitable for use in the invention are Enflurane, Sevoflurane and Desflurane.

According therefore to a first aspect of the present invention there is provided an analgesic anaesthetic composition comprising up to 50% v/v nitrous oxide, the balance being oxygen or other respirable gas mixture, characterised by the addition of an analgesically effective amount of an ether-based analgesic anaesthetic, said composition being disposable in a single container above its pseudo critical temperature at a pressure of 2000 psi, thereby to form a homogenous analgesic anaesthetic composition. Where the ether-based analgesic is isoflurane vapour the amount is preferably up to 0.4% v/v and most preferably between 0.25% and 0.325% v/v. With the higher percentages of isoflurane or of other ether-bases analgesic anaesthetics, the amounts of nitrous oxide may be commensurately reduced thus prolonging the period before serious amnesic or anaesthetic complications arise. When used in this context, "commensurate" refers to anaesthetic potency. Thus, for example, 50% nitrous oxide has the same potency as 0.6% isoflurane. Thus, if one added 0.3% isoflurane to a gaseous mixture, the nitrous oxide content could be reduced by half and the oxygen content would rise accordingly.

A further relatively minor problem with the utilisation of these ether-based analgesics such as isoflurane is caused by sputter which in theory could cause discomfort. Sputter occurs especially when the pressure drop from the storage container to a first stage reduction chamber in the demand regulator exceeds 62 bar or thereabouts. Sputter is manifested by rapid fluctuations of isoflurane concentration recorded by a gas analyzer measuring the delivered mixture. It is due to condensation and revaporisation of the isoflurane within the regulator or flow control valve. Although usually the sputter range is within clinically accentable limits and the average concentration per breath corresponds to the concentration within the pressurised supply container, there is a problem on cessation of inhalation that a small residue of condensate in the first stage reduction chamber vaporises to give a peak concentration in the next breath after the rest period. This may be alleviated by maintaining the pressure drop between the container and the first stage reduction chamber at a value of less than 62 bar; arranging that a 1 liter/minute gas bleed occurs from the first stage reduction chamber into the breathing circuit, by mechanically discarding or diluting the first breath after a rest period from the reduction chamber, or by using an absorbative system in the breathing circuit to take up liquidised ether-based analgesic such as isoflurane and then releasing it slowly. In practice however sputter has not yet demonstrated itself to be a clinical problem requiring solution.

Separation of the nitrous oxide and oxygen of Entonox can occur within the pressurized container if the container has been exposed to cold. In which case it is necessary to roll the container for 5–10 minutes after rewarming. The described composition may require more prolonged rolling.

According therefore to a further feature of the invention there is provided a method of filling a pressure cylinder with a medical gas composition which method comprises:
evacuating the cylinder to a significant negative pressure, partially filling the said pressure cylinder with said gas composition, cooling said partially said cylinder to a temperature below the liquification temperature of at least one of the components of said composition, and completely completing the filling process and allowing the cylinder to re-warm to room temperature, followed either by horizontal storage above 10° C. for about 48 hours, or followed by prolonged rolling.

In a preferred form of this aspect of the invention a higher molecular weight analgesic or anaesthetic adjunct for example an ether-based analgesic may be added after vacuum formation within the cylinder and prior to addition of the other components of gaseous admixture.

The invention will now be described, by way of illustration only, with reference to the following Examples.

EXAMPLE 1

Use of a Gas Composition According to the Invention

An analgesic anaesthetic gaseous composition comprising 50% v/v nitrous oxide, 0.25% v/v isoflurane and the balance of oxygen or other respirable gas (referred to hereinafter as Gas Mix A) was charged into a pressurized container as described in Example 3. This composition was administered during childbirth via a demand regulator in the usual way to a subject using the normal instructions given during the self-administration of Entonox.

It was found that the levels of analgesia were greater than would have been expected with Entonox.

EXAMPLE 2

Use of a Gas Composition According to the Invention

An analgesic anaesthetic composition of 30% v/v nitrous oxide, and 0.3% isoflurane the balance being of oxygen, was charged into a pressurised container as described in Example 3. This composition was self-administered during removal of chest drains in patients after surgery. In a small controlled study it was found that patients indicated a distinct preference for the composition in accordance with this example, rather than the control composition of Entonox without further additives.

EXAMPLE 3

Preparation of a Gas Composition According to the Invention

The production of the composition in accordance to the present invention may be effected as follows:

A gas storage cylinder having a safe working capacity of about 2000 psi was evacuated with a vacuum pump to a significant negative pressure of up to 30 inches/Hg. A measured quantity of isoflurane was injected by syringe into the cylinder whilst still under negative pressure. Nitrous oxide and oxygen was then added as percentages by weight until the cylinder was fully charged at 2000 psi. The gaseous composition was then used through the usual demand valve system as is done with Entonox administration. The cylinder so charged was used in Examples 1 and 2.

EXAMPLE 4

Use of Gas Mix A and Entonox in the Removal of Chest Drains

An analgesic anaesthetic gaseous composition comprising up to 50% v/v nitrous oxide, 0.25% v/v isoflurane and the balance of oxygen or other respirable gas (referred to hereinafter as gas mix A) was charged into a pressurised container as follows. 12 molybdenum steel cylinders were evacuated and liquid isoflurane injected into them sufficient to give a final concentration of 0.25% isoflurane. The cylinder was then filled to a pressure of 137 bar by decanting Entonox from high pressure cylinders in a two stage process. An initial fill brought cylinder pressure up to between 50 and 100 bar. The cylinder was then chilled to −40° C. allowing the nitrous oxide to liquefy and cylinder pressure to drop. Further Entonox was then added such that, when the cylinder returned to room temperature, a cylinder pressure of 137 bar was attained. Cylinders of gas mix A so prepared were then rolled to ensure complete mixing of the contents. The final gas mixture was analysed for oxygen (Taylor Servomex paramagnetic oxygen analyser) and for isoflurane (Datex Normal infra-red analyser) to ensure that target concentrations were achieved.

During surgery for coronary artery bypass grafting (CABG) two drains are placed to drain blood from the mediastinum and pericardial sac in the post-operative period and so to prevent cardiac tamponade and help detect undue bleeding. The drains exit below the costal margin on each side of the mid-line. The mediastinal drain passes up behind the sternum and is taken out to the right of the mid-line. The pericardial drain curves dorsally under the caudal surface of the heart within the pericardium and exits to the left of the mid-line. Both drains are about 300 mm in length and have the same diameter. These drains are generally removed on the second post-operative day after the patient's return to the thoracic high dependency ward from the intensive care unit. The removal of the drains is painful and within the Cardiothoracic Surgery Unit at Aberdeen Royal Infirmary for example, it has become standard practice for the nurse who is removing the drains to supplement analgesia by administering Entonox.

The analgesic efficacy of gas mix A was compared to Entonox in this study. The gas mixtures were self-administered by a demand valve system (Ohmeda), currently used for the administration of Entonox.

Gas Mixture Administration and Assessment of Analgesia

Prior to drain removal, the patient was allowed to breath gas, through a demand valve and facemask or mouth piece. The gas was breathed until the patient was observed to become drowsy and, in the opinion of the attendant staff, was adequately narcotised without being unconscious. This generally took about two minutes. The drain was then removed. The same procedure was repeated with the other gas after 10–15 minutes and the second drain removed. There was no attempt to fix which drain was removed first. The procedure was medically supervised for all patients in this trial although removal of such drains is usually a nursing procedure.

The patient's state of consciousness and degree of comfort were assessed before and during the procedure. Heart-rate, blood pressure and oxygen saturation (pulse oximetry were also noted before and after the removal of each drain. Scores for discomfort, sedation, co-operation and reaction to removal of the drain were also noted.

The patient was asked to complete a Patient Assessment Form after removal of each drain. The patient was asked to note the degree of pain caused by removal of the drain on a 100 mm linear analogue scale, to note whether the gas had a pleasant or unpleasant odour and whether any nausea was experienced. At the end of the procedure the patient indicated which gas was preferred and which drain removal was least painful.

Statistical analysis was performed using the computer program Minitab. Scores obtained while breathing the second gas mix were subtracted from those obtained for breathing the first gas mix. The resulting difference was analysed using a sign test (Minitab). Analogue pain scores were analysed differently. Paired scores obtained from patients breathing the first and second gas were compared using a Wilcoxon signed rank test. Comparisons between the group of patients breathing Entonox as first gas and the group breathing gas mix A as the first gas were made by Mann-Whitney tests. Comparisons were made both between gas mix A and Entonox and between data obtained during the first gas breathed and the second gas breathed.

35 patients were admitted to the trial; 15 receiving gas mix A as the first gas and 20 receiving Entonox as the first gas. Not all patients were able to provide complete sets of data and so 'n' is quoted for the statistics calculated. The results are shown in Table 1 below

TABLE 1

Pain scores (paired data only)

| Group | n | Median | Interquartile range 25% | 75% |
|---|---|---|---|---|
| Entonox for first drain | 13 | 10 | 5 | 23 |
| Gas mix A for second drain | 13 | 18 | 10.5 | 26.5 |
| Gas mix A for first drain | 12 | 15.5 | 4.75 | 23.75 |
| Entonox for second drain | 12 | 33.5 | 15 | 65 |
| First drain | 25 | 13 | 5 | 23.5 |
| Second drain | 25 | 25 | 12.5 | 38.5 |

Both Entonox and gas mix A were well tolerated by patients and there were no technical problems experienced during the trial. Both Entonox and gas mix A were detected as having an odour by some patients although in general neither were thought to have a smell and there was no overall difference between the two mixtures (n=35). There was no difference between the two mixtures or the order of gas administration with regard to the level of sedation (n=35), patient co-operation (n=35), reaction to removal of the drain (35), memory of drain removal (n=34), nausea (n=34) or dizziness (n=35). 6 patients had no memory of drain removal under gas mix A while 7 had no memory of events under Entonox.

There was no significant alteration in oxygen saturation, pulse rate or blood pressure due to removal of the drains and there was no change caused by changing the analgesic gas mixture.

Across both groups the removal of the second drain caused more discomfort (n=35, p 0.027) and the first gas administered was thought to be most helpful (n=30, p 0.013). Pain scores were also highest for the second drain (n=25, p 027) (Table 1).

When Entonox was administered for the first drain there was no difference in pain scores between the two gas mixtures (n=13 for both groups) (Table 1). When gas mix A was given for the first drain, pain score for the second drain was significantly higher (n=12 for both groups, p 0.028) (Table 1). Comparison between scores obtained while Entonox was being given showed that pain scores obtained while Entonox was given for the second drain were higher (n=15 and 14, p 0.005) (Table 2). Comparison between scores obtained while gas mix A was being given showed no difference. This is shown in Table 2 below

TABLE 2

Pain scores (all data)

| Group | n | Median | Interquartile range 25% | 75% |
|---|---|---|---|---|
| Entonox for first drain | 15 | 10 | 5 | 25 |
| Gas mix A for second drain | 15 | 17 | 6 | 25 |
| Gas mix A for first drain | 12 | 15.5 | 4.75 | 23.75 |
| Entonox for second drain | 14 | 38.5 | 21 | 65.25 |

The experimental design was chosen in the expectation that the painful stimulus elicited by the removal of each drain would be similar. This is not so with the data clearly showing that the second drain was more painful and that more help was obtained from the gas mixture during the first drain. The study does not offer an explanation of this phenomenon although several are possible. It may have been that there was a tendency for one or other of the two drains to be removed first and that the site of the drain influenced the pain suffered. Alternatively the experience of the first might have raised the expectation of pain for the second. Since the administration of the gas mixtures was controlled by the response of the patient it is unlikely that differences in gas uptake or distribution were of importance.

Comparison of Entonox and gas mix A indicate that while gas mix A controlled the pain of the removal of the second drain to a level similar to that of the removal of the first drain, this was not so for Entonox. When Entonox was given for the removal of the second drain, pain scores were higher than for any of the other three conditions during which pain scores were not dissimilar.

EXAMPLE 5

Use of a Gas Mix A and Entonox in Childbirth

An analgesic anaesthetic gaseous composition comprising up to 50% v/v nitrous oxide, 0.25% isoflurane and the balance of oxygen or other respirable gas (referred to hereinafter as gas mix A) was prepared as in Example 4.

The study describes the use of gas mix A in 56 women in labour. Ten of these participated in a trial comparing the efficacy of gas mix A as compared to Entonox and so there was no element of midwife or patient choice in the inhalational analgesic used apart from the mother consenting to participate in the study. In 46 women, however, choice of agent was left to the mother and midwife. Gas mix A and Entonox were self-administered by a demand valve system (Ohmeda), currently used for the self-administration of Entonox.

The use of gaseous analgesia was tested in the patients shown in Table 3 below.

TABLE 3

Summary of Patients

| | AGE (years) mean (range) | PARITY Primip | 2nd child | 3rd child | 4th child | Twins | Gestation (weeks) mean (range) |
|---|---|---|---|---|---|---|---|
| Free Study | 27.83 (16–39) | 27 | 9 | 9 | 1 | 2 | 39.5 (32–42) |
| Pilot Study | 27.30 (18–32) | 8 | | 2 | | | 39.8 (37–42) |
| All Mothers | 27.7 (16–39) | 35 | 11 | 9 | 1 | 2 | 39.6 (s.d. 1.87) |

56 mothers in total received gas mix A (table 3). 10 mothers received gas mix A as part of a pilot, prospective and controlled clinical trial studying the efficacy of gas mix A in comparison with Entonox. These were assessed as uncomplicated cases. 46 mothers received gas mix A as it was thought indicated by their attending midwife for the management of pain in labour and if gas mix A was available.

The Table 4 below shows the analgesic requirements of the patients. Usually, Entonox was the initial gaseous agent and gas mix A was offered as labour progressed.

TABLE 4

Summary of Gaseous Analgesic

| | Duration of Entonox hours, mean (range) | Duration of gas mix A hours, mean (range) | Intolerance to gas mix A (cases) |
|---|---|---|---|
| Free study | 3.58 (0–10) | 3.84 (0.2–10.98) | 3 |
| Pilot Study | — | 9.1 (3.17–14.12, n 10) | 0 |
| All Mothers | 3.58 (s.d. 2.45, n 45) | 4.77 (s.d. 3.52, n 56) | |

Five mothers who were started on gas mix A after a period of Entonox breathing reverted to Entonox. The reason for this was unrecorded in one instance and was due to the gas mix A running out in another. In one labour, a dose of opiate was given after gas mix A was started and this ameliorated pain such that Entonox was adequate thereafter. Of the remainder, one mother felt nauseated by gas mix A and the other did not like its smell. The level of intolerance to gas mix A was, therefore, in the order of 5% if it is assumed that the unrecorded reason for reverting to Entonox was gas mix A intolerance.

TABLE 5

Summary of opiate and regional analgesic requirements

| | One dose opiate | Two doses opiate | Three doses opiate | Epidurals | Epidural contra-Indicated |
|---|---|---|---|---|---|
| Free Study | 27 | 13 | 1 | 9 | 5 |
| Pilot Study | 7 | 1 | 0 | 0 | 0 |

59% of mothers received a single dose of opiate, which was either morphine or diamorphine, and 23% received two doses. A third dose of opiate was administered on only one occasion to a primigravid mother whose first stage lasted 22 hours and who did not want epidural analgesia.

In ten instances opiate was given before the start of gaseous analgesia and seven mothers required no opiate analgesic. In four cases the first dose of opiate was given with the start of inhalational analgesia. In the remaining mothers the first dose of opiate was given 0.3–8.12 hours (mean 2.25 s.d. 1.7) after the start of an inhalational analgesic.

Epidural analgesia was instituted in nine cases (16.1%). This compares with an epidural incidence of 16.1% deliveries in Aberdeen Maternity Hospital during the study period. In five cases the epidural provided adequate pain relief with no other form of analgesia being required. On four occasions, however, incomplete analgesia was obtained and inhalational analgesia was reintroduced with gas mix A being used twice under these circumstances.

This study shows that there were no unexpected problems with the administration of gas mix A and the level of intolerance was low. Undue drowsiness and lack of co-operation was not mentioned as a problem in the notes of the patient and in no case was the gas withdrawn because the midwife felt it unsafe to continue.

It was anticipated that gas mix A would only be used in more painful labours and after Entonox had been used. In this study, the conclusion was reached that gas mix A was used when pain ceased to be controlled adequately by Entonox and on occasion, even in place of an epidural analgesia. Thus in the free study, gas mix A was used without problem as a supplementary gaseous analgesic where a more potent agent was required than Entonox for 46 mothers. In a further 10 labours it was used without problem as the sole gaseous analgesic.

EXAMPLE 6

Stability of Gas Mix A at Low Temperatures in Storage

Gas mix A was prepared as described in Examples 4 and 5. The phase separation characteristics of a gas mix A at 137 bar was studied in respect of stability of isoflurane concentration with regard to cylinder temperature. Cylinder temperatures of down to −9.3° C. were studied.

The results showed that no separation was detected at a cylinder temperature of −3.3° C. Mild separation was seen at −4° C. and this was marked at −9.3° C. The lowest cylinder temperature likely to be encountered when used at room temperature is −3° C. amd thus it is concluded that phase separation will not be seen with a properly mixed cylinder in use.

I claim:

1. An analgesic anesthetic composition comprising up to 50% v/v nitrous oxide, an analgesically effective amount of an ether-based analgesic anesthetic selected from the group consisting of isoflurane, enflurane, sevoflurane, and desflurane and the balance being oxygen and another respirable gas disposed in a single container above its pseudo-critical temperature at a pressure of up to 2000 psi, thereby to form and maintain an analgesically effective homogenous composition in use.

2. A composition according to claim 1 wherein the ether-based analgesic is isoflurane vapour at an amount of up to 0.4% v/v.

3. A composition according to claim 2 wherein isoflurane vapour constitutes between 0.25% and 0.325% v/v of the admixture.

4. A method of minimizing fluctuations in the concentration of an analgesic anaesthetic composition administered from a pressurized container via a first stage reduction chamber, said composition comprising up to 50% v/v nitrous oxide, an effective amount of an ether-based analgesic anaesthetic selected from the group consisting of isoflurane, enflurane, sevoflurane, and desflurane and a balance of oxygen or other respirable gas mixture, which method comprises at least one of the following steps:

(I) maintaining the pressure drop between the container and a first reduction chamber at a value of less than 62 bar; or (II) arranging a 1 liter/minute gas bleed from the reduction chamber associated with the demand flow control mechanism, or (III) mechanically discarding or diluting the first breath after a rest period from the apparatus at the inception of inhalation; or (IV) using an absorbative system in the breathing system to take up any of said ether-based analgesic anaesthetic which has liquidized.

5. A method according to claim 4 wherein the ether-based analgesic anaesthetic is isoflurane.

\* \* \* \* \*